(12) United States Patent
Chiappo

(10) Patent No.: US 8,729,503 B2
(45) Date of Patent: May 20, 2014

(54) SYSTEM, METHOD AND APPARATUS FOR FORENSIC MARKING

(76) Inventor: Jorge G Chiappo, St. Petersburg, FL (US)

(*) Notice: Subject to any disclaimer, the term of this patent is extended or adjusted under 35 U.S.C. 154(b) by 228 days.

(21) Appl. No.: 13/282,618

(22) Filed: Oct. 27, 2011

(65) Prior Publication Data

US 2013/0110684 A1    May 2, 2013

(51) Int. Cl.
*C09K 11/00*    (2006.01)
*G01N 33/00*    (2006.01)
*G01N 21/64*    (2006.01)
*G01N 33/38*    (2006.01)

(52) U.S. Cl.
CPC ............. *G01N 33/383* (2013.01); *G01N 21/64* (2013.01); *C09K 11/00* (2013.01); *Y10S 428/913* (2013.01)
USPC ...................................... 250/458.1; 428/913

(58) Field of Classification Search
CPC ........ C09K 11/00; C09K 11/06; G01N 21/00; G01N 21/62; G01N 21/63; G01N 21/64; G01N 21/6428; G01N 21/6447; G01N 33/383
USPC ........ 106/712; 250/458.1, 459.1; 252/301.16, 252/301.4 R; 428/690, 913
See application file for complete search history.

(56) References Cited

U.S. PATENT DOCUMENTS 4,172,063 A * 10/1979 O'Brill ............................. 524/5
5,849,218 A * 12/1998 Johansen, Jr. et al. . 252/301.4 R
2003/0051638 A1 * 3/2003 Pomeroy ....................... 106/712

FOREIGN PATENT DOCUMENTS

WO    WO 2006128890 A1 * 12/2006

* cited by examiner

*Primary Examiner* — Mark R Gaworecki
(74) *Attorney, Agent, or Firm* — Larson & Larson, P.A.; Frank Liebenow; Justin P. Miller

(57) ABSTRACT

A forensic marker is disclosed including a marker that is added to the host material and is detectable for at least the expected life of the host material. The marker is inert with respect to the host material in that it does not significantly affect the desired qualities of the host material (e.g. weight, adhesive properties, structural integrity, etc). The marker is detectable, for example, by instruments, during the life of the host material.

9 Claims, 3 Drawing Sheets

SYSTEM, METHOD AND APPARATUS FOR FORENSIC MARKING

FIELD

This invention relates to the field of traceability and more particularly to a system and apparatus for identifying the origin of a host material long after the host material is deployed.

BACKGROUND

Often, construction materials for large projects are sourced from various suppliers. Each source is required to meet certain minimum specifications as required by the contractor. Once these materials are delivered to the job site and integrated into the construction, it is very difficult to determine the origin of the materials. For example, for a large project such as a dam, bridge, skyscraper, etc., concrete is often delivered to the job-site from several different cement companies. The concrete is poured and hardens. After the project is complete, it is very difficult to tell which sections of concrete were sourced from which companies. This is very frustrating when the final structure later fails due to cracking, delamination, spalling, discoloration, and/or surface dust formation. It has long been a burden of the courts to decide the origin of certain construction materials, typically after those materials fail.

For example, a company called M+P Labs provides forensic investigation of failed reinforced concrete. Their investigations help the courts decide if the failed concrete meets the concrete mix design, whether there were compatibility issues between the failed concrete and the environment, whether the water/cement ratio was correct, whether the concrete was placed correctly, finished correctly, and cured correctly. This company provides these services for several reasons, such as to determine blame when the concrete fails. For example, was the failure due to the mixing or placement of the concrete, placing blame on the contractor. Or was the concrete mix the cause, placing the blame on the concrete manufacturer. Such an investigation is often difficult when the job is large and a contractor hires subcontractors, each subcontractor providing mix from a different cement plant. Once the cement is mixed and poured, it is often difficult to determine the origin of each concrete section. Consider a roadway in which rectangular slabs are poured from a series of cement trucks. The first slab is poured with cement from company 'a,' the second from company 'b,' the third and fourth section from company 'a,' and the fifth from company 'c.' Now, consider that after 10 years of use the third slab begins to delaminate, and a delaminated section is lifted by a truck and injures a pedestrian. The injured hires a forensic company to determine if company 'a,' 'b,' 'c,' or an engineering company is responsible for the delamination and, hence, the injury. Since the rectangular slabs are all made of concrete with substantially the same ingredients, it is very difficult to determine the origin of any particular slab. Since it is so difficult to determine, at times, the wrong company is charged with responsibility.

To protect from being wrongly assessed with blame for materials provided, many companies need a way to positively identify their materials, even years after their materials have been used in construction projects.

In a similar scenario, a bonding agent is used, for example, to bond stucco to a surface. Later, when the bonding agent fails and the stucco peels from the underwall, the origin of the bonding agent is needed to determine who will be responsible for repairs.

Another example has to do with toxic waste. When a conscientious company needs to dispose of toxic waste, that company hires a disposal company who is believed to be responsible and will dispose of the waste properly. Unfortunately, there have been examples of improper disposal such as dumping 55 gallon drums of toxic waste in bodies of water. When these drums are discovered, there is presently little evidence to track the toxic waste back to the origin and to determine who is responsible for the improper disposal and resulting pollution.

Litigation costs for such activities are often extremely expensive and, a wrongfully accused company often expends hundreds of thousands of dollars defending itself from wrongful claims and law suits.

What is needed is a system that will provide positive identification as to the origin of a material.

SUMMARY

A forensic marker includes a marker (item or material) that is added to the host material and is detectable for at least the expected life of the host material. The marker is inert with respect to the host material in that it does not significantly affect the desired qualities of the host material (e.g. weight, adhesive properties, structural integrity, etc). The marker is detectable, for example, by instruments, during the life of the host material.

In one embodiment, a forensic marker is disclosed including a marker that is detectable for at least the expected life of a host material. The marker is added to the host material but does not significantly affect the desired qualities of the host material. The marker being inert to the host material (e.g., the marker does not substantially alter the physical performance of the host material) and is detectable during the life of the host material.

In another embodiment, a method of determining the origin of a host material is disclosed including adding a marker to the host material. A specific attribute of the marker is assigned to an origin of the host material (e.g. the manufacturer). The marker is detectable for at least the expected life of the host material and the marker is inert to the host material (e.g. does not significantly affect the physical properties of the host material). Furthermore, the marker is only detectable with instrumentation during the life of the host material. The method continues with deploying the host material with marker (e.g. delivering cement with embedded markers). When identification of the origin of the host material is needed, identifying the specific attribute of the marker using the instrumentation.

In another embodiment, a forensic marker is disclosed. The forensic marker is added to a host material and includes a marker that, after being added to a host material, is detectable with instrumentation for at least the expected life of the host material into which the marker is added. The marker is inert with respect to the host material, and, the marker is not detectable by the naked eye under ambient conditions.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
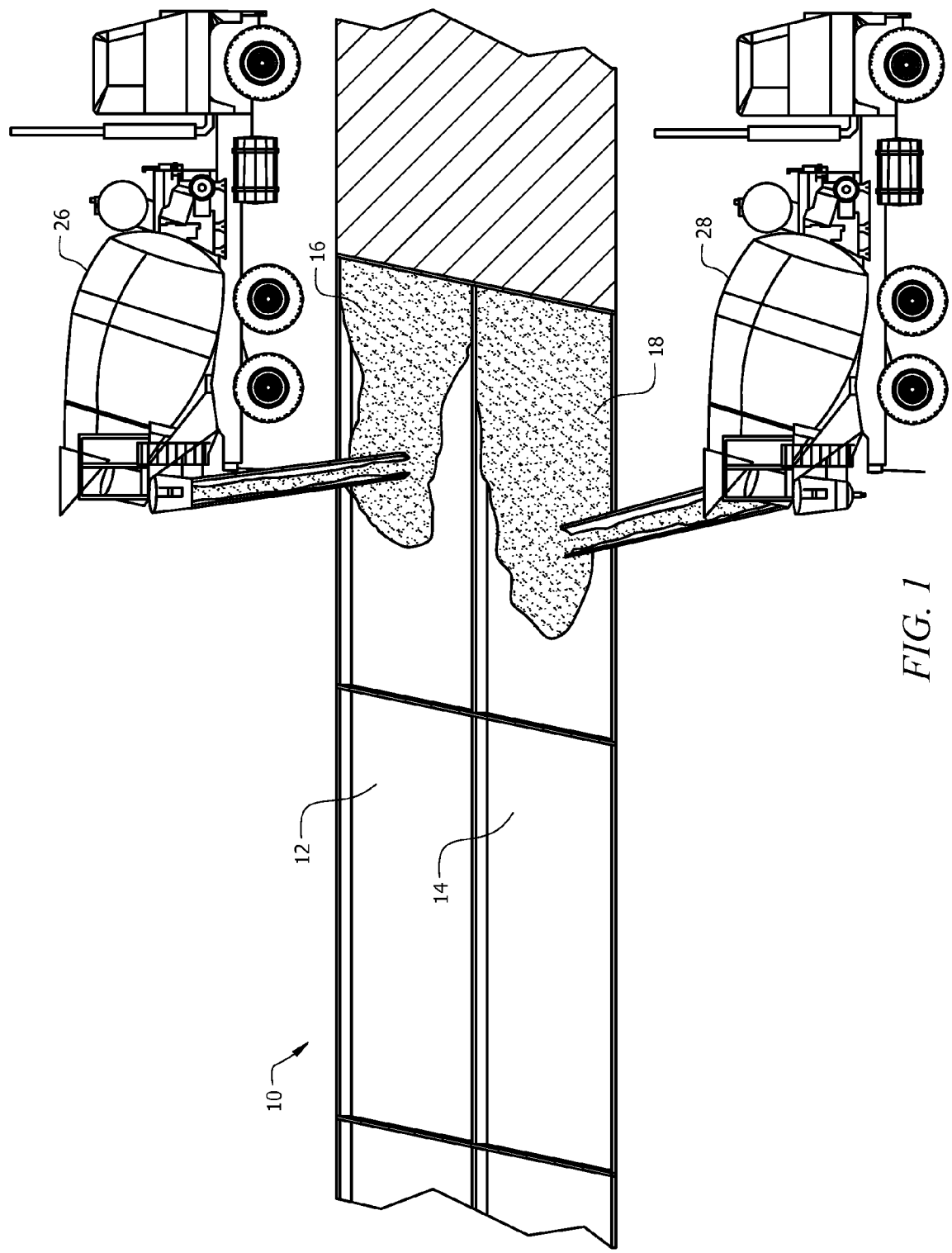
FIG. 1 illustrates a perspective view of a construction site.

Reference will now be made in detail to the presently preferred embodiments of the invention, examples of which are illustrated in the accompanying drawings. Throughout the following detailed description, the same reference numerals refer to the same elements in all figures. The forensic markers are described in an exemplary scenario as forensic markers for concrete/cement (cementitious materials) and hazardous waste, though many other uses of the forensic markers are anticipated including, but not limited to, bonding agents, sheet rock, security paper, etc.

Throughout, the term "inert" refers to the marker as not significantly affecting the physical properties of the host material. Note that the addition of any material to a host material will, at least, slightly affect the physical properties of the host material, but the markers disclosed here within are selected to minimally affect the physical properties of the host material, not affecting the performance of the host material in any significant way. Therefore, the markers preferably do not significantly alter the chemical composition of the host material, the structural strength of the host material, the adhesive properties of the host material, the drying time of the host material, etc.

It is anticipated that in an exemplary use of forensic markers, the forensic marker is be added to any form of host material such as (but not limited to) stucco, concrete, mortar, the tile grout, cements, etc. Once added, the forensic marker becomes an agent used to identify the architects, engineers and specifiers of different products that go into these host materials. Examples of different products that go into the host material are reinforcements fibers for stucco, concrete etc, bonding agents, water repellents, water reducers, and all other add mixtures. By adding forensic markers that identify the components of the host material, if there is ever a problem, the architect, engineers and specifiers, are able to identify the products that were used on the job and compare them to the products that were specified for the job. This will save thousands of dollars on laboratory tests and legal fees etc by a simple test at the job site.

Additionally, forensic markers are also useful for retail packaged products. In such, the source materials in the retail packaging include appropriate forensic markers to later identify the source of the materials after the materials are used for a project. For example, a particular home supply store has its own brand of cement mix, packaged in 80 pound bags. Because of the weight, each local home supply store provides packages marked with the home supply store's brand to local cement companies and the local cement companies fill the packages with cement. Therefore, when purchasing such packages of cement, one cannot easily ascertain the company of origin. By having each cement company add forensic markers, the origin of the cement is easily identified long after the cement is used, even if the user did not save the packaging or note the manufacturer. Again, this is but an example of one use of forensic markers.

Referring to FIG. 1 a perspective view of a construction site 10 is shown. Again, use of the forensic markers with a cementitious material is but one example of a use for forensic markers as discussed above.

In this example, a roadway 10 is being poured in sections or slabs 12/14/16/18. Some slabs 12/14 have already been poured, troweled and textured while other slabs 16/18 are being poured from trucks 28/28. A first slab 16 is being poured from a first truck 26 while a second slab 18 is being poured from a second truck 28. Since many cubic feet of concrete is used for such construction, often the trucks 26/28 come from two or more cement factories/companies. In this example, assume that the first truck 26 is from a first cement company (not shown) and the second truck 28 is from a second cement company (not shown). This practice is typical and there are typically no records maintained that cross-link the individual slabs 12/14/16/18 to the origins of the host materials used. Therefore, once the roadway 10 is complete, there is no way to determine the origin of the cement used in each slab 12/14/16/18. In most cases, this is not an issue unless something goes wrong and the cement fails. For example, if the cement in the first slab 16 begins to delaminate 5 years after the roadway 10 is complete, there may be some liability for such premature failure. In the above example, it would be difficult to determine the origin of the cement used in the first slab 16, and therefore, difficult to place liability on the first cement company.

Prior to the disclosed invention, it was often difficult or impossible to determine the origin of any host materials after construction was complete. Even if some sort of recording was attempted during construction, records are often not well kept. For example, in the above scenario, the arrival time of delivery trucks 26/28 (cement trucks) is not predictable, making it an almost impossible task to keep track of which truck 26/28 poured which slab 12/14/16/18.

By adding a forensic marker to each manufacturer's raw material (e.g. concrete), the origin of each host material is traceable years after the construction is complete. Consider a forensic marker for concrete that is a color. One manufacturer adds red dye and another adds blue dye. Should the concrete fail, the forensic marker provides a way to positively determine the source of the concrete by the color (red, blue, or purple if both were mixed). Although color is one potential forensic marker, color is not always practical because it is desirable that, although the forensic marker is inert in that it does not noticeably change the properties of the host material (e.g. construction material such as cement), it is preferred that the forensic marker not visually alter the host material. In the present example, one wouldn't want a road that has alternating red and blue slabs 12/14/16/18.

By requiring the manufacturer of a given host material to include a forensic marker, it becomes a much easier operation to identify the origin of the host material many years after the host material is deployed. In the example above, if each cement plant in a geographic area is assigned one particular forensic marker and required to add that forensic marker to all cement produced in that plant, cement from that plant is discernable many years after it is put into use.

It is preferred that the forensic marker does not significantly alter the host material. Although color is used as a first example of a forensic marker, the added coloring alters the look of the host material (the appearance of the host material to the naked eye of a person). It is preferred that the forensic marker is not detectable by sight, instead requiring some other detection system such as magnification or instrumentation.

One such example of a forensic marker is a Radio Frequency Identification capsule added to the host material. Years later, using an RFID scanner, one is reliably able to determine the origin of the host material by scanning the host material with an RFID scanner. Each manufacturer is assigned one RFID number, or a range of RFID numbers, such that the manufacture is determinable based upon the number from the scanned RFID(s). Instruments such as standard RFID scanners are used to later determine the origin of the host material by reading the RFID value from the RFID(s) within the host material. In some embodiments, the RFID is coated/encapsulated in a material such as plastic, glass, etc., to seal the RFID from corrosion or any interaction with the host material and/or the environment.

It is also preferred that the forensic marker be inert and not significantly affect the performance of the host material. Likewise, it is preferred that the host material not significantly affect the forensic marker. It is also preferred that the forensic marker have sufficient longevity as to last at least as long as the expected life of the host material.

Another exemplary forensic marker is one or more chemical compounds that are not typically found in the host material and that is/are inert with respect to the host material, is/are not degraded by the host material and is/are detectable for years after the host material is deployed. In such, to determine the origin of the host material, the host material is chemically analyzed to determine which of the marker chemicals are present. Using concrete as an example, one manufacturer adds a small percentage of a polymer to their concrete and another manufacture adds a small percentage of zinc. Years after the concrete is deployed, spectral analysis of the concrete will show the polymer marker for the first manufacturer, or the zinc marker for the second manufacturer.

Another forensic marker is one or more florescent markers such as fluorescent polyamide fibers. Such markers are not visible until exposed to ultraviolet light. When excited by ultraviolet light, the florescent markers glow with different colors similar to how florescent paint glows with different colors under ultraviolet light (a.k.a. black light). With florescent markers, it is anticipated that one manufacturer is assigned a single color or a combination of colors and another manufacturer is assigned a different color or a different combination of colors, providing sufficient permutations for the given application. For example, the first manufacturer is assigned orange and purple, the second is assigned orange and green and the third is assigned purple and green. Years later, when the origin of a section of the host material is needed, the host material is exposed to an appropriate light source (e.g. UV light) and the colors of the markers indicate the source of the host material. Because the markers are anticipated to be small, it is anticipated that in some cases instrumentation such as magnification is required (e.g. use of a microscope). Also, in some applications of forensic markers, because of the sheer number of sources of the host material either country-wide or world wide, it is anticipated that the permutations of marker distinctions provide enough unique forensic markers to distinguish origins within the region. For example, using the fiber colors orange, purple, and green from above and a geographic region of a city, 7 permutations are provided (orange, purple, green, orange-purple, orange-green, purple-green, and orange-purple-green). If there are more sources of the host material than 7, either a different color need be added (e.g. red) or a second shape or thickness of fluorescent polyamide fiber need be added. For example, having 2-micron fibers and 4-micron fibers, provides many more permutations.

Another forensic marker is an inert material in the shape of a fiber, or other shape such as a sphere, cube, rod, pyramid, etc. One example of this is rayon fibers. The rayon fibers are relatively small (e.g. similar to human hair), have a color, and a defined cross-sectional diameter. After adding the rayon fibers to the host material, the fibers are detectable by viewing the host material under magnification (e.g. under a microscope). As an example, using cement as a host material, the first manufacturer is assigned orange and purple fibers of 150 micrometers, a second manufacturer is assigned orange and green of 150 micrometers, and a third manufacturer is assigned orange and green or 100 micrometers. Years later, when origin of a section of the solidified cement is needed, a cross section of the solidified cement is viewed under magnification and the color of the fibers and/or the diameter of the fibers provides evidence of the origin of the cement in question.

In some uses of forensic markers, other geometric attributes are varied to provide even more variations. For example, a forensic marker is added to liquid toxic waste that is disposed in 55 gallon drums 40 (see FIG. 2). The forensic marker must not be significantly affected by the toxic waste. If the toxic waste is acidic, the forensic marker must not dissolve in the toxic waste. Therefore, for acidic toxic waste, glass is one potential forensic marker that will not be dissolved by the acidic toxic waste. In this example, several shapes and sizes of glass are added to the toxic waste 40 to identify the origin of the toxic waste. For example, one company that has toxic waste for disposal is required to add forensic markers comprising glass fibers that are colored green, are 200 microns long and 100 microns thick. Another company is required to add markers comprising glass balls that are colored red and are 200 microns thick. If toxic waste is found improperly disposed, analysis of the toxic waste will show the presence of one of the forensic markers, leading the authorities to the source of the toxic waste and, eventually, to the disposal company that failed to properly dispose of the toxic waste.

Another forensic marker is an inert, metallic fiber of a specific size (e.g. length and diameter). It is well known that metallic fibers have a resonant frequency where the fibers resonate at one particular radio frequency. In this example, one manufacturer adds fibers that resonate at a first frequency and another manufacturer adds fibers that resonate at a second frequency. Years later, when the origin of a section of the host material is needed, an instrument is exposes the host material (with markers) to a sweep frequency. During this sweep the power absorbed by the metallic fibers within the host material is monitored to determine which fibers are present in the host material. Any number of metallic fiber sizes or combinations of fiber sizes is anticipated. For example, one manufacturer combines fibers that resonate at frequencies F1, F2 and F3 and another manufacturer uses fibers that resonate at frequencies F1, F3 and F4, etc. Any metal is anticipated, but for many host materials, a corrosion-resistant metal is preferred such as steel, zinc, etc. Alternately, any metal is used for the metallic fiber and the metallic fiber is coated/encapsulated in a material such as plastic, glass, etc., to seal the metallic fiber from corrosion by the host material and/or the environment.

Another forensic marker is an inert, low-radiation-dosage decaying material such as a radioactive material. The energy that is being emitted by the material (marker) is detected by an instrument (e.g. by a Geiger counter) to determine the type and/or combination of forensic marker and, hence, the source of the host material.

Many examples of forensic markers are described above for use in marking many suitable host materials for later identification. The use of any number of markers alone or in combination with other markers is fully anticipated. For example, it is anticipated that one class of host material be marked with fluorescent markers in combination with resonant metallic markers, thereby providing either a greater number of combinations of unique overall markers and/or providing a redundant, more reliable marker.

Although the above examples show how the forensic markers are used with cement, many uses of the forensic markers are anticipated, including, but not limited to hazardous waste, bonding agents, sheet rock, security paper, insulation, paint, medicine, asphalt, raw plastic, etc.

It is anticipated that an authority will be deployed to manage the forensic markers across given industries or categories. For example, a forensic marker authority of cement is anticipated. This authority will have a set of forensic markers suitable for introduction into any cementitious material such as concrete, stucco, cinder blocks, etc. This authority will assign and track the various markers to various companies based upon geography, such that there is little or no ambiguity as to the origin of any finished product throughout that geography. In this, the authority will have a fixed set of permutations of forensic markers and manage assignment of each permutation such that, within each geographic area and within each product category, no two companies use the same forensic marker permutation. The management of the forensic markers is desired to provide positive correlation between deployed host materials and the manufacture of the deployed host materials.

Figure 2:
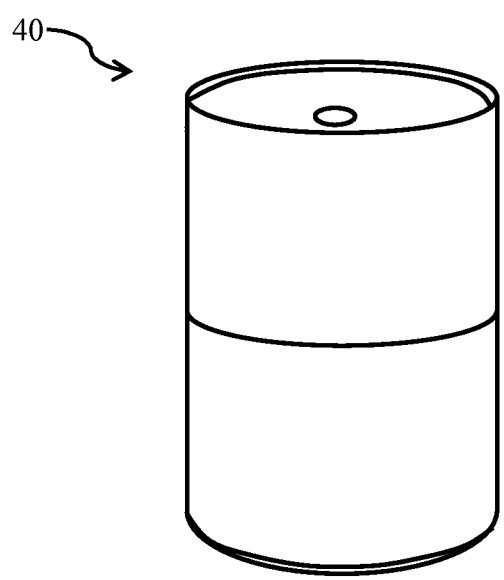
FIG. 2 illustrates a perspective view of hazardous waste.

Referring to FIG. 2, a perspective view of a typical hazardous waste 40 is shown. This is another example of a use for the forensic markers. As an example, a first company has a manufacturing facility, a byproduct of which is a liquid hazardous waste 40. The first company contracts with a second company to properly dispose of the hazardous waste 40, but the second company finds it is too expensive to properly dispose of the hazardous waste, so the second company transfers the hazardous waste 40 into unmarked containers and deposits the containers in the ocean. Years later, the containers are discovered, lying on the bottom of the ocean. Without a forensic marker, there is no foolproof way to provide positive traceability back to the origin of the hazardous waste 40, the first company, and there is no way to trace the path of the hazardous waste 40 from the first company to the second company to penalize the second company and prevent future occurrences.

By adding forensic markers to the hazardous waste 40, authorities will easily determine the origin of the hazardous waste 40 and are provided the ability to find the companies involved in this crime. For example, any company producing hazardous waste is required to add forensic markers, such as Radio Frequency Identification (RFID) devices into the hazardous waste 40, each RFID uniquely identifying the company of origin.

Being that many hazardous waste 40 materials are caustic, it is fully anticipated that the forensic marker is not negatively affected by the hazardous waste 40. One example of such is RFID tags encapsulated in glass to insulate the electronics of the RFID tag from the caustic host material. Another example of such is using glass formed in certain geometric shapes and having certain sizes. In the first example, when unlawfully dumped hazardous waste 40 is uncovered, an RFID scanner is used to identify the RFID tags and, therefore, the source of the hazardous waste 40. In the second example, when unlawfully dumped hazardous waste 40 is uncovered, the hazardous waste 40 is examined under magnification to locate and measure the shape and size of the geometric glass forensic markers and, therefore, the source of the hazardous waste 40. For example, one company adds glass forensic markers shaped as two-micron wide spheres and another company adds glass forensic markers shaped as three-micron pyramids.

Figure 3:
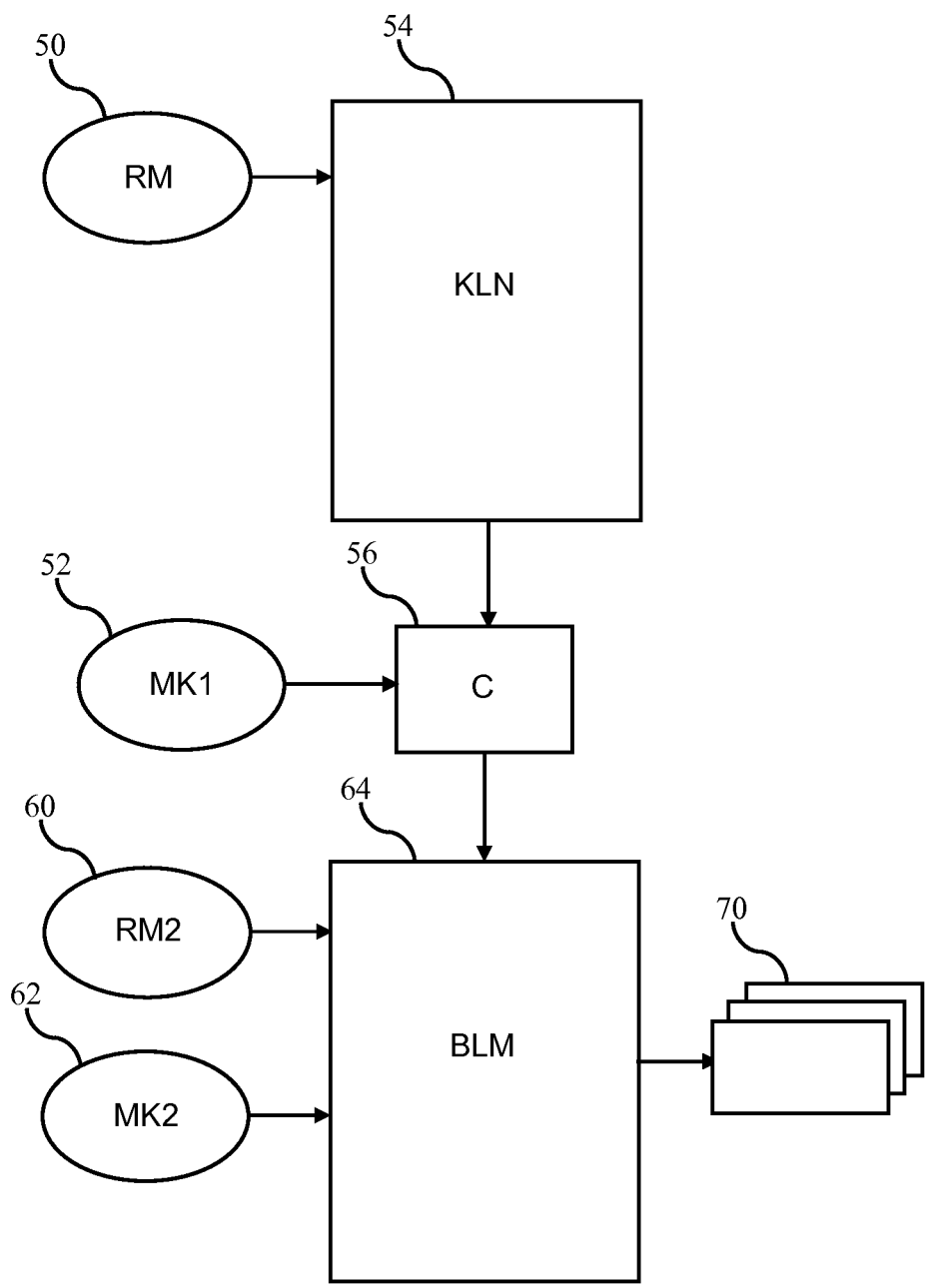
FIG. 3 illustrates a block diagram of a manufacturing operation.

Referring to FIG. 3, a block diagram of a manufacturing operation is shown. Again, the example shown relates to cementitious materials and is used as an example as the forensic markers are anticipated for use with many other types of materials and are in no way limited to use with cementitious materials.

In this example, raw materials 50 (e.g. calcium carbonate and silica-bearing minerals) are introduced into a kiln 54 to produce cement 56. In the kiln 54, the raw materials (e.g. calcium carbonate and silica-bearing minerals) are heated to form a mixture of calcium silicates that are then ground into the resulting cement 56. A first marker 52 is added to the cement 56 to identify the manufacturer of the cement 56.

The cement 56 is transported to a second manufacturer 64, for example a concrete brick manufacturer 64. The second manufacturer 64 adds additional raw materials 60 to the cement 56 and a second marker 62 and produces a final product 70 (e.g. concrete blocks 70).

Although two manufacturers 54/64 are shown, any number of manufactures is anticipated in the production chain, including one manufacturer. Since each manufacture 54/64 adds their forensic marker to their output product 56/70 (e.g. marker-1 52 is in cement 56 and both marker-1 and marker-2 are in blocks 70), the final product (e.g. blocks 70) will contain forensic markers 52/62 that will identify both the manufacturer 54 of the cement 56 and the block manufacturer 64. In this way, if the blocks 70 are used in construction and fail, the forensic markers 52/62 provide evidence as to the origin of the blocks, including both the manufacturer 54 of the concrete 56 and the manufacture 64 of the block 70.

In the example above, the markers 52/62 are anticipated to be distinguishable from each other. For example, if the first manufacturer 54 adds an assigned marker 52 that uniquely identifies the first manufacture 54 among other similar manufacturers in a geographic region, the second manufacturer 64 must add a marker 62 that is unique across other manufactures of that product across the same geographic region as well as across the manufacturers that are similar to the first manufacturer.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A forensic marker for adding to a host material, the forensic marker comprising:
   a marker that is detectable for at least the expected life of a host material into which the marker is added, the marker is inert with respect to the host material, the marker is detectable during the life of the host material;
   wherein the marker is fluorescent fibers, each fluorescent fiber emitting a specific color of light in response to exposure to ultra-violet light;
   wherein the fluorescent fibers comprise more than one type of fluorescent fibers, each of the more than one type of fluorescent fiber emitting a different color of light responsive to exposure to ultra-violet light.

2. A forensic marker for adding to a host material, the forensic marker comprising:
   a marker that is detectable for at least the expected life of a host material into which the marker is added, the marker is inert with respect to the host material, the marker is detectable during the life of the host material;

wherein the marker is inert fibers, each inert fiber having a specific color and cross-sectional diameter;

wherein the inert fibers are made of rayon.

3. A forensic marker for adding to a host material, the forensic marker comprising:

a marker that is detectable for at least the expected life of a host material into which the marker is added, the marker is inert with respect to the host material, the marker is detectable during the life of the host material;

wherein the marker is metallic fibers; and wherein the metallic fibers are detected by measuring a resonance of the metallic fibers to a range of radio frequencies.

4. A method of determining the origin of a host material, the method comprising:

adding a marker to the host material, one or more specific attribute of the marker is/are assigned to an origin of the host material, the marker is detectable for at least the expected life of the host material, the marker is inert to the host material, the marker is only detectable with instrumentation during the expected life of the host material;

recording a correlation between the one or more specific attributes of the marker and the origin of the host material;

deploying the host material with marker; and when identification of the origin of the host material is needed, identifying the specific attribute of the marker using the instrumentation and using the correlation between the one or more specific attributes of the marker and the origin of the host material;

wherein the marker is fluorescent fibers, each fluorescent fiber emitting a specific color of light responsive to exposure to ultra-violet light and the instrumentation is a source of ultraviolet light coupled to a magnification system.

5. A method of determining the origin of a host material, the method comprising:

adding a marker to the host material, one or more specific attribute of the marker is/are assigned to an origin of the host material, the marker is detectable for at least the expected life of the host material, the marker is inert to the host material, the marker is only detectable with instrumentation during the expected life of the host material;

recording a correlation between the one or more specific attributes of the marker and the origin of the host material;

deploying the host material with marker;

when identification of the origin of the host material is needed, identifying the specific attribute of the marker using the instrumentation and using the correlation between the one or more specific attributes of the marker and the origin of the host material;

wherein the marker is metallic fibers; and wherein the metallic fibers are detected by measuring a resonance of the metallic fibers to a range of radio frequencies.

6. A forensic marker, the forensic marker added to a host material, the forensic marker comprising:

a marker that, after being added to a host material, is detectable with instrumentation for at least the expected life of the host material into which the marker is added, the marker being inert with respect to the host material, and, the marker is not detectable by the naked eye under ambient conditions;

wherein the marker is fluorescent fibers, each fluorescent fiber emitting a specific color of light in response to exposure to ultra-violet light and the instrumentation is a source of ultraviolet light and a magnification system.

7. The forensic marker of claim 6, wherein each fluorescent fiber has a specific color and/or cross-sectional diameter.

8. The forensic marker of claim 7, wherein the inert fibers are made of rayon.

9. A forensic marker, the forensic marker added to a host material, the forensic marker comprising:

a marker that, after being added to a host material, is detectable with instrumentation for at least the expected life of the host material into which the marker is added, the marker being inert with respect to the host material, and, the marker is not detectable by the naked eye under ambient conditions;

wherein the marker is metallic fibers; and wherein the instrumentation is a device that exposes the metallic fibers to a range of radio frequencies and the device measures the resonance of the metallic fibers to the range of radio frequencies.

\* \* \* \* \*